United States Patent [19]

Johnson

[11] Patent Number: 5,443,468

[45] Date of Patent: Aug. 22, 1995

[54] METHOD FOR DRILLING A BORE IN BONE USING A COMPACTION DRILL

[76] Inventor: Lanny L. Johnson, 4528 S. Hagadorn Rd., East Lansing, Mich. 48823

[21] Appl. No.: 191,610

[22] Filed: Feb. 4, 1994

[51] Int. Cl.$^6$ ............................................. A61B 17/56
[52] U.S. Cl. .................................. 606/80; 606/102
[58] Field of Search ................. 606/80, 79, 84, 85, 606/96, 99, 102, 105, 170, 180; 623/13; 408/1 R, 207, 209, 226, 229, 230; 433/165, 166; 33/511, 512

[56] References Cited

U.S. PATENT DOCUMENTS

| | | | |
|---|---|---|---|
| 4,524,766 | 6/1985 | Petersen | 606/184 X |
| 4,590,928 | 5/1986 | Hunt et al. | 606/80 X |
| 4,710,075 | 12/1987 | Davison | 408/202 |
| 5,108,405 | 4/1992 | Mikhail et al. | 606/96 |
| 5,122,134 | 6/1992 | Borzone et al. | 606/80 |
| 5,180,384 | 1/1993 | Mikhail et al. | 606/80 |
| 5,354,300 | 10/1994 | Goble et al. | 606/80 |

OTHER PUBLICATIONS

Hudson, William Henry "A New Method of Performing Operations of the Skull" *Surgery, Gynecology and Obstetrics*, Feb. 1910, pp. 1–4.

*Primary Examiner*—Stephen C. Pellegrino
*Assistant Examiner*—Guy V. Tucker
*Attorney, Agent, or Firm*—Cushman Darby & Cushman

[57] ABSTRACT

A drill bit is provided that is constructed and arranged to form a bore in a bone by cutting and moving bone fragments to a wall of the bore. The drill bit includes an elongated shaft having a distal portion and a proximal portion. The proximal portion has a constant diameter. A cutting tip is defined at the free end of the distal portion. A segment of the distal portion has transverse cross-sectional area less than that of the proximal portion. The distal portion segment also includes a surface to facilitate movement of the bone fragments towards the proximal portion of the shaft. When the drill bit enters the bone so as to form the bore and is moved an amount such that the distal portion is disclosed completely within the bore, a space is defined between the wall of the bore and a periphery of the segment of the distal portion which receives the bone fragments. Further insertion of the drill bit into the bone causes the bone fragments to move along the surface of the distal portion segment to the outer cylindrical surface of the proximal portion which compacts the bone fragments against the wall of the bore.

2 Claims, 5 Drawing Sheets

METHOD FOR DRILLING A BORE IN BONE USING A COMPACTION DRILL

BACKGROUND OF THE INVENTION

1. Field of the Invention

The present invention relates to fixation of a tendon/bone graft during a surgical procedure and particularly, to the formation of a bore in bone used in anchoring the bone/tendon graft.

2. Description of Related Art

Anterior cruciate ligament reconstruction includes replacing the ligament with a tendon/bone graft. During arthroscopic knee surgery, for example, a surgeon can form a tunnel through the tibia, intra articular joint and femur to receive a bone-tendon-bone graft. The graft must be adequately secured. Typically this is accomplished by tying sutures over ligament buttons, or by using staples, unicortical screw posts or interference screws.

One conventional method of fixation of a tendon/bone graft is to harvest a plug from the patellar tendon. Each plug of the bone-tendon-bone graft is harvested typically in semi-circular cross-section with a semi-circular gouge and is conventionally sized. Next, as shown in FIG. 1, a graft socket 400 is drilled into bone 410 with a conventional twist drill bit 420 which breaks-up bone fragments 430 and discharges those fragments from the socket 400. The bone fragments 430 are extracted from the socket since they move along the helical groove 440 of the drill bit 420 until the fragments exit the socket, as shown by the arrows F in FIG. 1. The plug is then inserted into the socket and fixed therein, preferably by a screw. The sockets created during the conventional extraction drilling process are thin-walled, having open, exposed marrow elements, which limit the likely success of the mechanical fixation of the graft, since the chances of screw migration, divergence, and convergence are increased.

SUMMARY OF THE INVENTION

The preferred and exemplary embodiment of the present invention includes a drill bit for forming a bore in a bone and simultaneously compacting the bone fragments against the wall of the bore. In accordance with the principles of the present invention, the drill bit includes an elongated shaft having a distal portion and a proximal portion. The proximal portion has a constant diameter. A cutting tip is defined at the free end of the distal portion of the shaft. The cutting tip is joined with the proximal portion by a segment of the distal portion which has a transverse cross-sectional area less than that of the proximal portion. The distal portion segment includes a surface to facilitate movement of the bone fragments towards the proximal portion of the shaft. When the drill bit enters the bone to form the bore and reaches a position wherein its distal portion is disposed completely within the bore, a space is defined between the wall of the bore and the periphery of the segment the distal portion which is of lesser cross-sectional area than the bit's proximal portion. Bone fragments removed during drilling are retained in the space. Further insertion of the drill bit into the bone causes the bone fragments to move along the distal portion towards the proximal portion. The proximal portion has a periphery constructed and arranged to compact the bone fragments against the wall of the bore, thereby thickening and strengthening the bore wall.

A further aspect of the present invention is a method for forming a bore in bone which includes the steps of initiating a bore in bone utilizing a drill bit, advancing the drill bit further into the bone to lengthen the bore, preventing fragments of the bone created by advancing the drill bit from exiting the bore by trapping the bone fragments between a wall of the bore and a periphery of a segment of the drill bit, advancing the drill bit further into the bone so that a shaft portion of the drill bit compacts the bone fragments against a portion of the bore wall, thereby thickening the portion of the bore wall, and removing the drill bit from the bore.

With the foregoing in mind, other objects, features and advantages of the present invention will become more apparent upon consideration of the following description and appended claims with reference to the accompanying drawings, all of which form a part of this specification.

DESCRIPTION OF THE PREFERRED EXEMPLARY EMBODIMENTS

Figure 1:
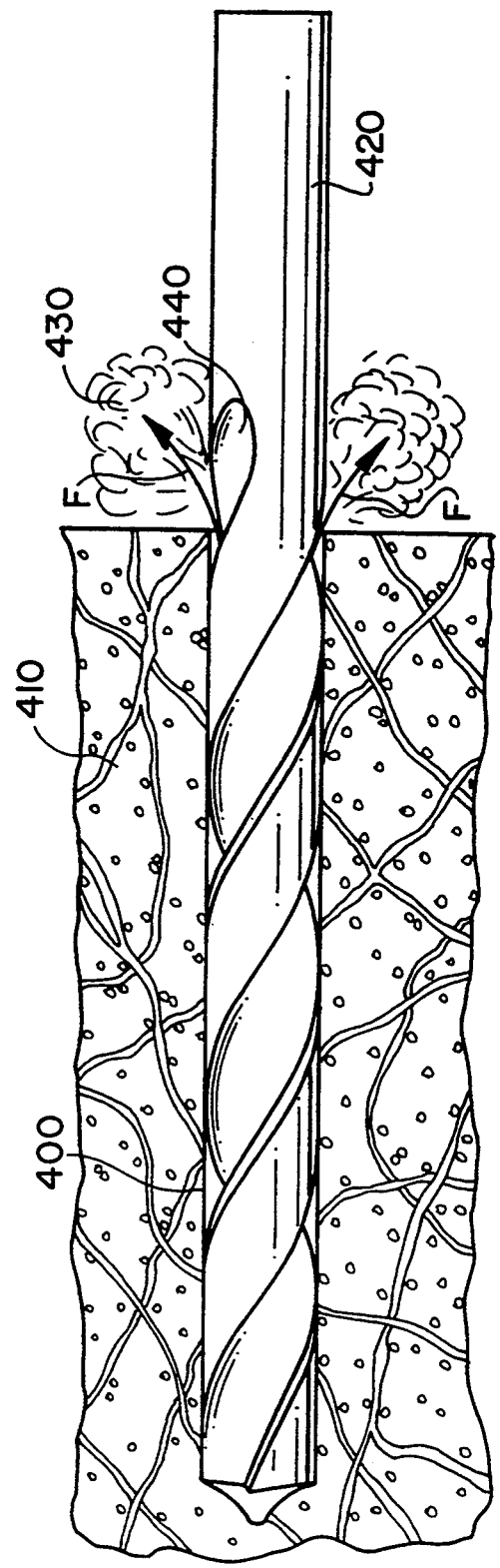
FIG. 1 is a side elevational view of a conventional twist drill bit shown creating a bore in a bone by conventional extraction drilling.
Figure 2:
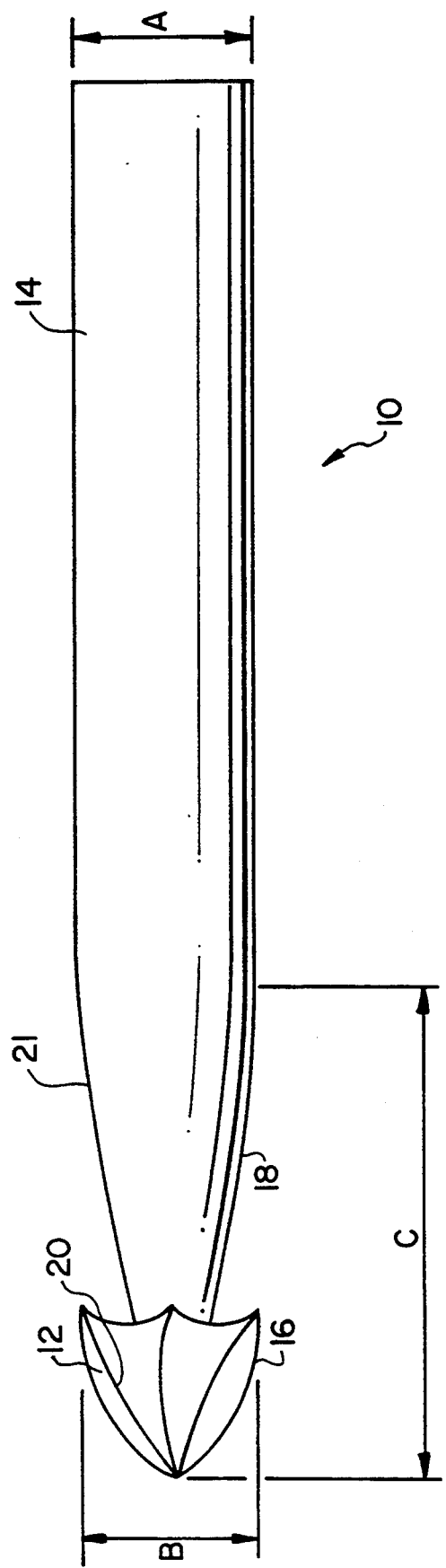
FIG. 2 is an enlarged side elevational view of a compaction drill bit according to the present invention.

FIG. 2 shows a compaction drill bit, generally indicated at 10, provided in accordance with the principles of the present invention. The drill bit 10 includes an elongated shaft having a distal portion 12 and a proximal portion 14. The proximal portion 14 has a constant diameter A and merges with the distal portion 12. A cutting tip 16 is defined at the free end of the distal portion. A maximum diameter B of the cutting tip 16 is substantially equal to diameter A of the proximal portion 14.

As shown in FIG. 2, a segment 18 of the distal portion 12 has a diameter which gradually increases from where it joins the tip 16 towards the location where segment 18 merges with proximal portion 14. Thus, segment 18 includes transverse cross-sectional areas which are less than the maximum cross-sectional area of the tip 16 or that of the proximal portion 14. The purpose of this feature will become apparent below. In the illustrated embodiment, the tip 16 at the distal portion 12 is of conventional acorn-shape having a pointed end. A plurality of cutting edges 20 are disposed about the periphery of the tip 16. The total length C of the distal portion 12 is approximately 1 to 2 centimeters.

Figure 3:
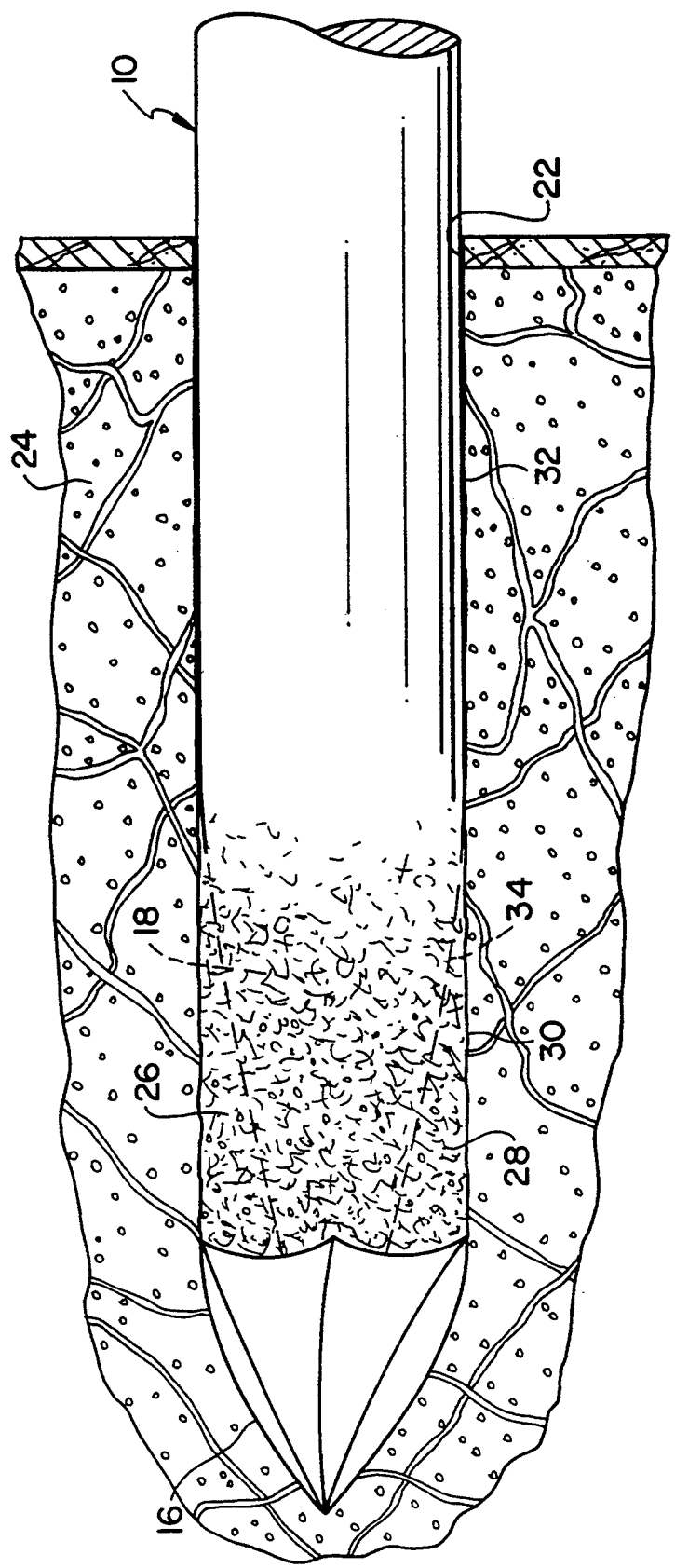
FIG. 3 an enlarged side elevational view of the compaction drill bit of FIG. 2, shown creating a bore in bone by compaction drilling in accordance with the invention.

With reference to FIG. 3, the compaction drill bit 10 illustrated in FIG. 2 is shown forming a bore 22 in bone 24. Rotation of the drill bit 10 causes bone fragments 26 to be cut by the cutting tip 16 entering the bone. As the drill bit 10 is advanced to lengthen the bore, the bone fragments 26 collect in the space 28 defined between wall 30 of the bore and the periphery 34 of segment 18 of the distal portion 12. Since the proximal portion 14 has a diameter substantially equal to that of the bore 22, the bone fragments 26 are trapped in space 28 and cannot escape from the bore 22, as in conventional extraction drilling.

The segment 18 of distal portion 12 has a tapered surface 21 (FIG. 2) which directs bone fragments 26 towards the proximal portion 14. As the drill bit 10 is advanced within the bone 24, the bone fragments 26 directed towards the proximal portion 14 by surface 21 are compacted against the wall of the bore 30 as they are contacted by the outer cylindrical surface of the proximal portion 14 of bit 10. The continued penetration of the rotating proximal portion 14 smooths and compacts the bone fragments 26 to create a thickened bore wall 32 from the drill bit 10 entry site to the extent that portion 12 extends within the bore 22.

Figure 4:
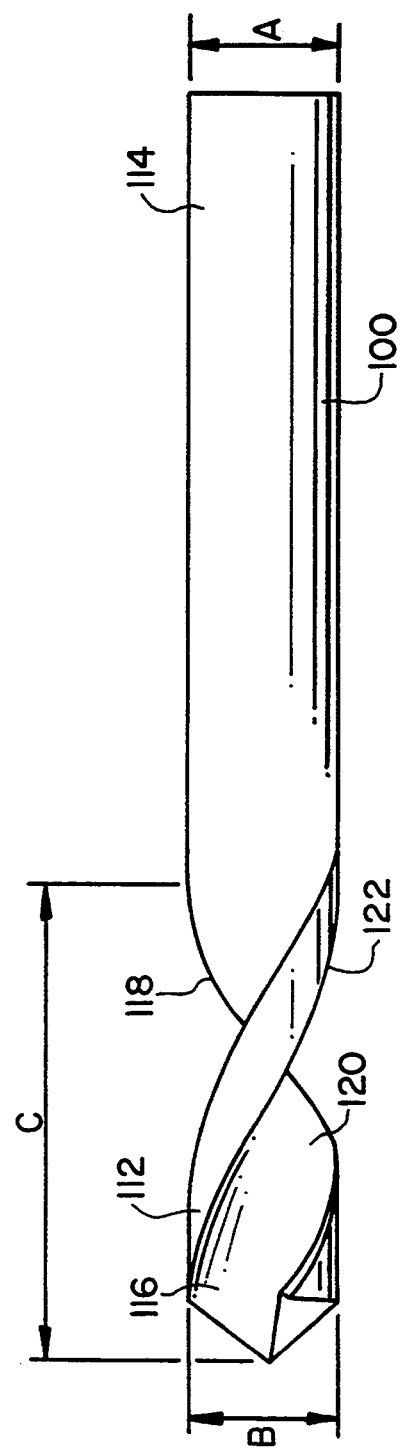
FIG. 4 is an enlarged side elevational view of a second embodiment of a compaction drill bit according to the present invention.

Another embodiment of a compaction drill bit according to the invention is shown in FIG. 4. As shown, the compaction drill bit 100 includes an elongated shaft having a distal portion 112 which merges with a proximal portion 114. The proximal portion 114 has a constant diameter A. A cutting tip 116 is defined at the free end of the distal portion, the tip having a maximum diameter B which is substantially equal to diameter A of the proximal portion 114. The distal portion is formed with a cutting element 122 which defines a helical groove 120. The length C of the distal portion is approximately 1 to 2 centimeters. When the distal portion 112 is entirely within a bore drilled in a bone, a space exists between the groove 120 and the wall of the bore. As is the case with the embodiment of FIG. 2, this space provides a collection chamber to trap the fragments of cut bone. The cutting element 122 of distal portion 112 directs the bone fragments towards the proximal portion 114 of the shaft during drilling so that, as explained above, the bone fragments are compacted by the outer cylindrical surface of the proximal portion 114 so as to thicken the bore wall.

Figure 5:
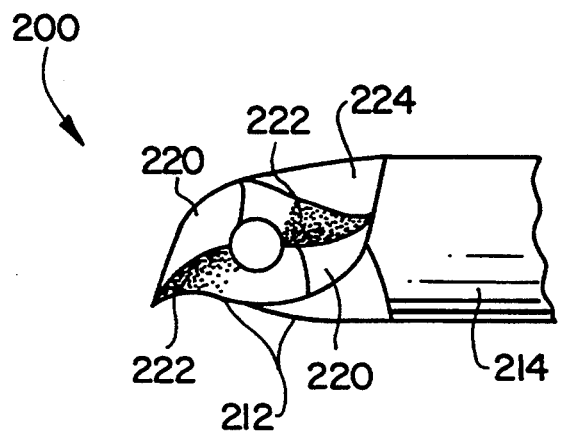
FIG. 5 is an enlarged perspective view of a distal portion of a third embodiment of a compaction drill bit provided in accordance with the principles of the present invention.
Figure 6:
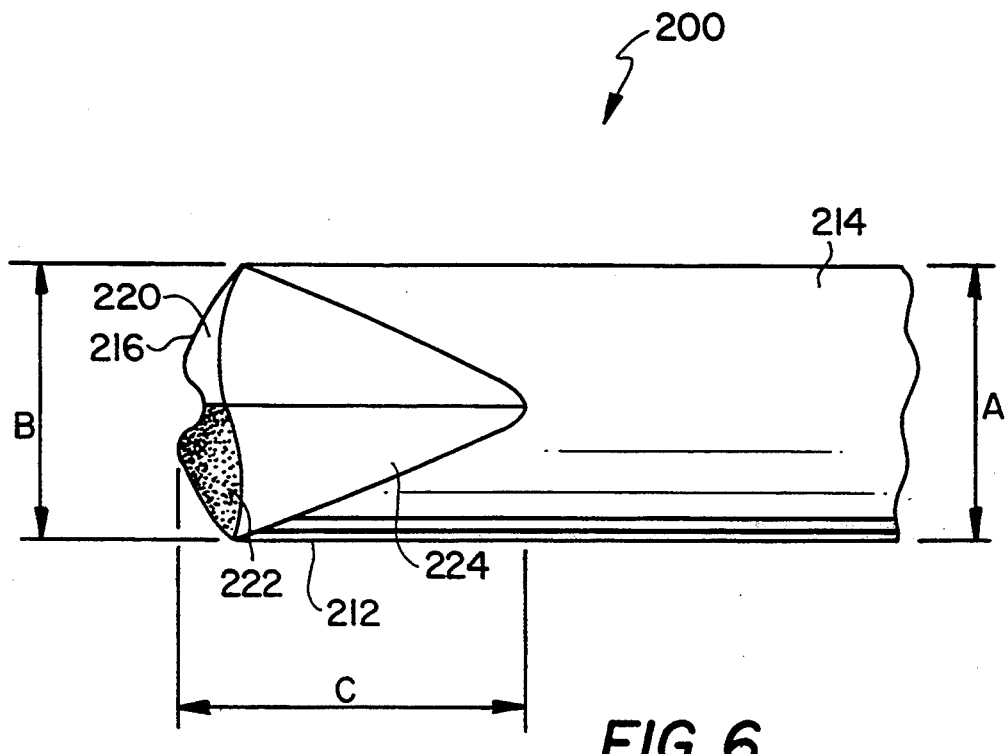
FIG. 6 is an enlarged side elevational view of the compaction drill bit of FIG. 5.

A third embodiment of the drill bit according to the present invention is shown in FIGS. 5 and 6. More particularly, the compaction drill bit 200 includes an elongated shaft having a distal portion 212 and a proximal portion 214. The proximal portion 214 has a constant diameter A and merges with the distal portion 212. A cutting tip 216 is defined at the free end of the distal portion 212, with a maximum diameter B thereof being substantially equal to diameter A of the proximal portion 214. The tip 216 includes a concave surface 220 for cutting harder bone, such as the cortical bone, prior to entering softer cancellous bone. The cutting tip 216 also includes a convex surface 222 which moves softer bone to surface 224 of the distal portion 212. Surface 224 defines a recessed segment of distal portion 212 which is deepest at the tip 216 and gradually decreases in depth until it merges with the proximal portion 214. As in the previous embodiments, the length C of the distal portion is approximately 1–2 centimeters.

When the drill bit 200 is employed to form a bore in bone, the concave surface 220 removes bone as fragments, and the convex surface 222, together with surface 224, move the bone fragments to the outer cylindrical surface of the proximal portion 214 where the bone fragments are compacted against the bore wall to thicken the wall, as explained above.

It can be appreciated that a variety of cutting tips may be employed in accordance with the principles of the present invention. A bore formed by the compaction drilling method of the present invention has denser and thicker bore wall than a bore formed by conventional extraction drilling.

Drills according to the present invention may be used to compact soft or hard bone. Moreover, a series of drill bits having gradually increasing diameters may be used to form the bore, rather than using one drill bit of the desired diameter as described above.

Once the formation of a bore by compaction drilling is accomplished, the end of the tendon/bone graft may be disposed in the bore and a screw or the like may be used to secure the end of the graft to the bone. The compacted wall of the bore provides enhanced resistance to pull-out of a screw or other fixation device used to secure the graft. Fixation strength is increased since bone has a memory, i.e., as it is displaced by compaction, the bone has a tendency to return to its previous position and thus, securely hold the fixation device. Further, the bone is thicker at the bore walls than is normal for cancellous bone. Thus, stronger fixation is achieved since greater torque may be employed when inserting the fixation device.

When comparing the biological fixation of a tendon/bone graft using a bore formed by the compaction drilling method of the present invention and one formed by conventional extraction drilling, it has been observed that when formed by the extraction drilling method, wherein bone fragments are removed from the bore, the bore was lined with fibrous tissue three weeks after the procedure. Moreover, the bone was not in contact with the inserted graft, and the walls of the bore were thin and broken and adjacent bone marrow was fatty and not reactive. In comparison, a bore formed by the compaction drilling method showed no fibrous tissue lining after three weeks. The bone was in direct and complete contact with the graft, and the walls of the bore were substantially thicker than the walls of a bore formed by the extraction drilling method. Additionally, the adjacent bone marrow was proliferative.

After six weeks, the bore formed from the extraction drilling method still had a fibrous lining, although the bone reacted to form better contact around the graft than at three weeks. The adjacent bone marrow has reacted. In comparison, the bore formed by the compaction drilling method showed thick bone surrounding the device six weeks after the procedure. The walls were thicker than walls of the bore formed by the extraction method, and the marrow was reactive.

After nine weeks, the bore formed by extraction drilling appeared the same as it was at six weeks. However, the bore formed by compaction drilling showed secondary biological proliferation of bone around the bore, increasing the bone thickness by enchondral ossification.

The above-described methods of forming a compacted bore in bone have may uses. For example, as discussed above, the methods may be utilized to fix screws in bone for such procedures as cortical cancellous hip fractures, fractures and graft fixation. The methods may also be used with screws combined with rods or plates. The methods of forming compacted bores of the invention are suitable for joint replacement, such as total hip replacements, total knee replacements, total elbow replacements and total wrist replacements. Further, the methods may be utilized in bone grafting procedures for the following conditions: osteochondritis dissecans; osteonecrosis; and fractures, such as depressed tibial plateau, hip, intra-articular fractures, non-union fractures or mal-union fractures. The methods also may be employed in marrow stimulation, such as treatment of myeloblastic disease, bone marrow transplants, autoimmune disease, cancer treatments such as leukemia, anemias, growth factors, growth hormones, tissues stimulation factors, and in cell culture procurement. Other uses of compacted bores are enchondral ossification, such as bone grafting, bone growth factors, bone stimulation factors and bone transplantation.

It will be appreciated that the compaction drilling method of the present invention may be used in conjunction with devices such as those disclosed in applicant's U.S. patent application Ser. No. 08/328,137, filed on Oct. 24, 1994, which is a continuation of Ser. No. 08/111,970 filed on Aug. 26, 1993 (now abandoned), which is a continuation of Ser. No. 07/848,546 filed on Mar. 9, 1992, (now abandoned), which is a divisional of U.S. Pat. No. 5,116,337, issued on May 26, 1992, the disclosures of which are hereby incorporated hereinto by this reference. For example, the bone surrounding the graft socket or bore 22 (FIG. 3) may be further compacted and enlarged by inserting a sizing instrument having a larger diameter than the selected drill bit 10 into the bore 22. The appropriate sizing instrument preferably is tubular with a blunt forward end having rounded edges. A blunt forward end is preferable since compaction at the bottom of the bore may thus be accomplished. Once the appropriate bore size is obtained, a bone plug may be inserted into the bore, for example, in a bone tendon/bone graft and secured by a screw or the like.

It will be appreciated that drill bit of the invention, and its use in forming a bore in bone, provide a bore having a thickened wall for increased mechanical fixation. Of course, the drill bit may be manually or motor operated.

While the invention has been described in accordance with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims, which scope is to be accorded the broadest interpretation of such claims so as to encompass all such equivalent structures.

What is claimed is:

1. A method of forming a bore in bone comprising the steps of:

initiating a bore in said bone utilizing a drill bit of the type comprising an elongated shaft having a cylindrical proximal portion of substantially constant diameter and cross-sectional area and a distal portion, said distal portion including a cutting element at a free end thereof and a segment having varying cross-sectional area less than that of said proximal portion, said segment joining the cutting element to the proximal portion and increasing in cross-sectional area between said element and the proximal portion;

advancing said drill bit further into the bone to lengthen the bore and move fragments of bone, created by advancing the drill bit, to said segment of varying cross-sectional area thereby retaining said bone fragments between a wall of the bore and said segment;

further advancing said drill bit into the bone whereby additional creation of bone fragments causes retained fragments to be moved against the wall of the bore and forced between the wall and said proximal portion whereby the bone fragments are compacted against and along a portion of the wall to increase the density of said portion of the wall; and removing said drill bit from said bore.

2. A method of forming a bore in bone according to claim 1, further comprising the step of:

additionally compacting and enlarging the bore following removal of the drill bit by inserting into the bore a sizing instrument having a larger diameter than that of said drill bit.

* * * * *